United States Patent
Ohashi et al.

(10) Patent No.: US 7,037,301 B1
(45) Date of Patent: May 2, 2006

(54) DISPOSABLE ABSORBENT WEARING ARTICLE AND PROCESS FOR PLACEMENT OF ELASTIC MEMBERS ASSOCIATED WITH LEG HOLES ON THE ARTICLE

(75) Inventors: Naoto Ohashi, Kagawa (JP); Nariaki Shimoe, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 710 days.

(21) Appl. No.: 10/088,662

(22) PCT Filed: Sep. 21, 2000

(86) PCT No.: PCT/JP00/06480

§ 371 (c)(1),
(2), (4) Date: Jul. 29, 2002

(87) PCT Pub. No.: WO01/21124

PCT Pub. Date: Mar. 29, 2001

(30) Foreign Application Priority Data

Sep. 21, 1999 (JP) .......................................... 11-267691
Sep. 7, 2000 (JP) ..................................... 2000-272169

(51) Int. Cl.
*A61F 13/20* (2006.01)

(52) U.S. Cl. .................................................. 604/385.27

(58) Field of Classification Search ............................................. 604/385.24–385.29
See application file for complete search history.

(56) References Cited

U.S. PATENT DOCUMENTS 6,905,565 B1 * 6/2005 Shimoe ....................... 156/161
2002/0193775 A1 * 12/2002 Shimoe ................. 604/385.27

* cited by examiner

*Primary Examiner*—Larry I. Schwartz
*Assistant Examiner*—Ginger Chapman
(74) *Attorney, Agent, or Firm*—Butzel Long

(57) ABSTRACT

A disposable body fluid absorbent wearing article such as a disposable diaper includes elastic members 12 associated with leg-holes each having a plurality of elastic members which are placed along cutouts of side flaps 6 to surround a wearer's thighs. The elastic members 12 associated with the leg-holes are converged into respective single bundles along first elastic zones S of a crotch region 10 and diverged in second and third elastic zones F, B extending forward and backward from the first elastic zones S so that the elastic members 12 associated with the leg-holes may have a tensile stress not higher along the first elastic zones S than in the second and third elastic zones F, B.

4 Claims, 4 Drawing Sheets

DISPOSABLE ABSORBENT WEARING ARTICLE AND PROCESS FOR PLACEMENT OF ELASTIC MEMBERS ASSOCIATED WITH LEG HOLES ON THE ARTICLE

TECHNICAL FIELD

This invention relates to disposable absorbent wearing articles such as a diaper, a pad for incontinent or a sanitary napkin and a process for placement of elastic members associated with leg-holes on such articles.

BACKGROUND ART

The invention relating to such articles, particularly to such article provided along respective thigh-surrounding zones with a plurality of rubber threads as elastic members associated with leg-holes and the invention relating to a process for placement of these rubber threads are disposed in Japanese Patent Application Nos. 1992-122257A and 1992-317650A. The process for making the disposable diaper is generally classified into a process according to which the thigh-surrounding zones of individual finished products extend in the machine direction (so-called lengthwise or end-to-end arranged process) and a process according to which the thigh-surrounding zones of individual finished products extend in the direction orthogonal to the machine direction (so-called laterally running or side-by-side arranged process). The inventions disclosed in the above-cited Applications are classified into the former process. Generally, the former process is suitable for making a so-called open-type diaper having its front and rear waist regions connected to each other immediately before actual use to meet requirements for mass-production of the diaper at desired high velocity. The latter process, on the other hand, is suitable for making a so-called pants-type or pull-on-type diaper having its front and rear waist regions previously connected to each other. The invention relating to the latter process in which a plurality of elastic members are preferably placed along each of the thigh-surrounding zones is disclosed in Japanese Patent Application No. 1991-33201A.

The above-cited Japanese Patent Application Nos. 1992-122257A and 1992-317650A disclose the process for placement of continuous elastic members associated with the leg-holes. According to this process, a continuous web as a component material for the diaper is provided along its transversely opposite side edges with adhesive zones arranged intermittently in the longitudinal direction, then elastic members associated with the respective leg-holes, each comprising a plurality of elastic elements, are fed under tension onto the respective adhesive zones and secured thereto so that the elastic members associated with the leg-holes may describe generally sinusoidal curves. According to this process of prior art, these elastic members associated with the leg-holes are forcibly traversed against tensile force of these elastic members so as to extend across the continuous web. Consequently, the elastic members associated with the leg-holes present a tensile strength higher in a generally middle zone than the remaining zone in a crotch region of the diaper.

Placement of the elastic members associated with the leg-holes in this manner causes these elastic members to present a tensile stress higher in the middle zone than in the remaining zone, resulting in that gathers formed in the middle zone of the crotch region do not easily extend as the diaper is worn. Gaps between the wearer's skin and the gathers may cause leak of body fluids. Additionally, it is likely that the diaper as a whole might shift from its proper position and a liquid-absorbent core might be twisted and deformed as the crotch region of the diaper shifts due to a movement of the wearer's thighs. These factors also may cause leak of body fluids and, in addition, might create a feeling of discomfort against the wearer. In case of a diaper provided on its side flaps on which the elastic members associated with the leg-holes are placed and these side flaps are provided, in turn, with elastic barrier flaps, there is an additional anxiety that relatively high tensile stress of the elastic members associated with the leg-holes might prevent the barrier flaps from rising as sufficiently high as expected.

It is an object of this invention to solve such problems as have been described above in disposable absorbent wearing articles such as a disposable diaper.

DISCLOSURE OF THE INVENTION

According to this invention, there is provided a disposable absorbent wearing article having a longitudinal direction and a transverse direction orthogonal to the longitudinal direction, the article comprising an absorbent structure including a liquid-pervious topsheet, a liquid-impervious backsheet, a liquid-absorbent core disposed therebetween and a pair of side flaps extending outward from transversely opposite side edges of the core, a plurality of elastic members associated with leg-holes being placed on cutouts formed in the side flaps to surround the thighs of a wearer.

The disposable absorbent wearing article further comprising the plurality of elastic members associated with leg-holes are converged substantially into respective single bundles along first elastic zones each extending over a given length of the crotch region in the longitudinal direction of the article and are spaced one from another along second and third elastic zones extending from the first elastic zone along respective side edges of the front and rear waist regions over a given length and the elastic members associated with the leg-holes present a tensile stress not higher in the first elastic zone than in the second and third elastic zones and said first, second and third elastic zones of said elastic members associated with the leg-holes are contiguous one to another.

According to another aspect of this invention, there is provided a process for placement of elastic members associated with leg-holes on a disposable absorbent wearing article, comprising the steps of:
(a) feeding a continuous web as a component of the article in its longitudinal direction at a given velocity and at the same time continuously coating the continuous web along its transversely opposite side edges extending its longitudinal direction with a hot melt adhesive to form first and second adhesive zones;
(b) feeding first and second continuous elastic members associated with the leg-holes, each comprising a plurality of continuous elastic members spaced one from another and under tension, onto the first and second adhesive zones, respectively, in such a manner that the first and second elastic members associated with the leg-holes may extend across the first and second adhesive zones of the continuous web beyond respective inner and outer side edges of the first and second adhesive zones and respectively describe generally sinusoidal curves about the respective adhesive zones with respective first zones of the first and second elastic members associated with the leg-holes lying on the first and second adhesive zones being fixed to the first and second adhesive zones, respectively, and respective second zones of the first and second elastic members associated with the leg-holes extending beyond inner side edges of the first and second adhesive zones being contractibly shifted to the first and second adhesive zones so as to be fixed to the first and second adhesive zones, respectively; and (c) cutting the continuous web along lines extending in its transverse direction across respective third zones of the first and second continuous elastic members associated with the leg-holes together with the first and second continuous elastic members associated with the leg-holes so that thereupon the third zones may contract.

The invention includes the following embodiments:

The core has a stiffness of 1–30 gf·cm (10–300 mN·cm) in the longitudinal and transverse directions.

The elastic members associated with the leg-holes are respectively spaced in the first elastic zones from the side edges of the core at least by 10 mm. According to still another preferred embodiment of this invention relating to the article, the elastic members associated with the leg-holes in the second and third elastic zones are progressively diverged as these elastic members extend in the front and rear waist regions.

The process further includes the steps of placing liquid-absorbent cores on given zones on the continuous web defined between the first and second adhesive zones at given intervals in the longitudinal direction of the web and placing and bonding second continuous web upon and to the first continuous web so as to cover the liquid-absorbent cores.

The first and second adhesive zones are formed by continuously coating the transversely opposite side edges of the first continuous web with hot melt adhesive so as to describe a plurality of spirals extending in the longitudinal direction of the first continuous web.

The first continuous web is made of liquid-impervious material and the second continuous web is made of liquid-pervious material.

PREFERRED EMBODIMENTS OF THE INVENTION

Embodiments of this invention will be described in more details with reference to the accompanying drawings.

Figure 1:
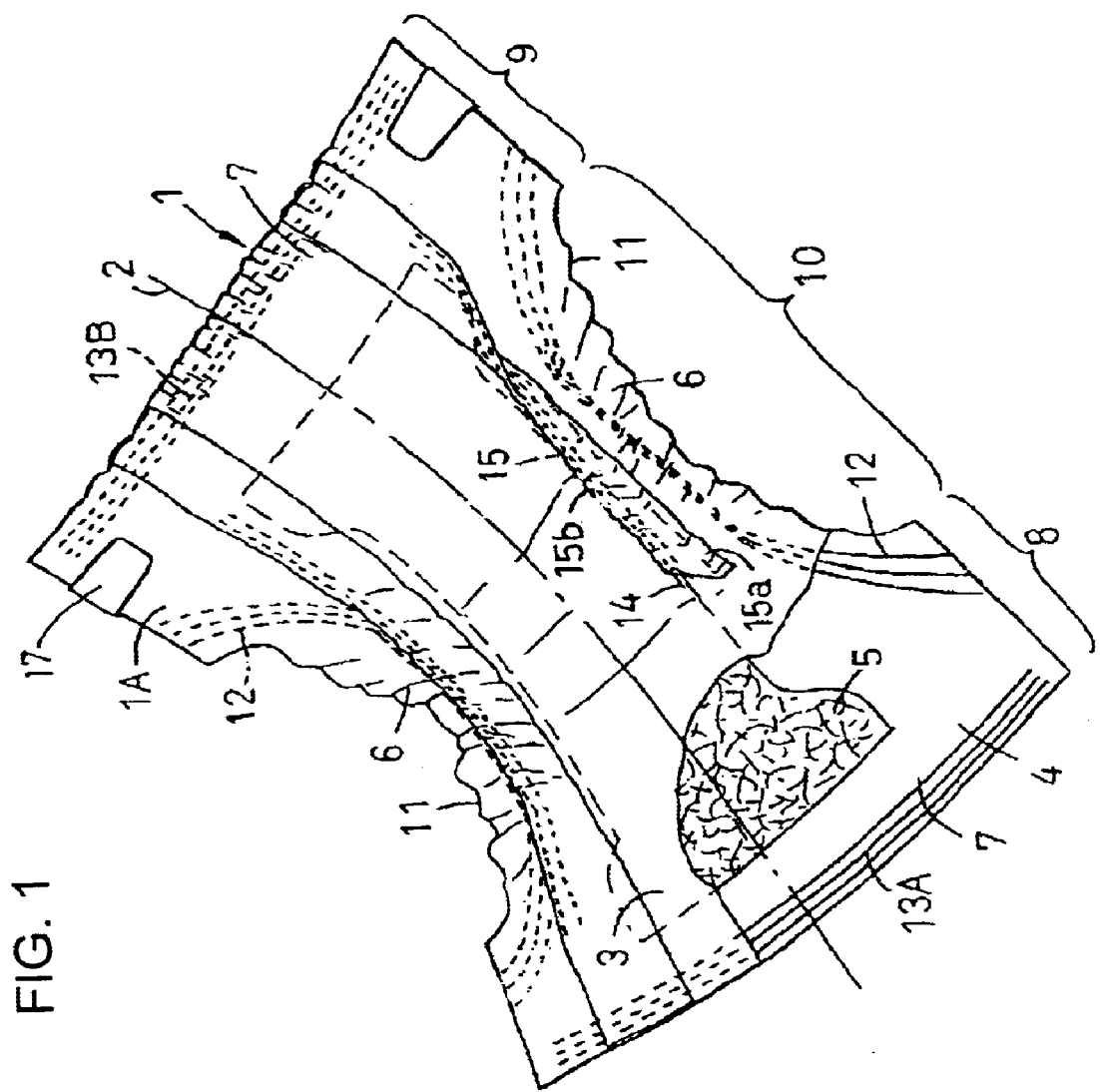
FIG. 1 is a partially cutaway perspective view showing a disposable diaper.

(1) A diaper as one embodiment of a disposable absorbent wearing article according to this invention:

Referring to FIG. 1, a diaper as a specific embodiment of a disposable absorbent wearing article has a longitudinal center line 2 and provided with an absorbent structure 1A. The diaper 1 has a longitudinal direction and a transverse direction orthogonal to this longitudinal direction. The absorbent structure 1A has its side halves symmetric about the longitudinal center line 2, and comprises a liquid-pervious topsheet 3, a liquid-impervious backsheet 4, a liquid-absorbent core 5 interposed between these sheets 3, 4, a pair of side flaps 6 and a pair of end flaps 7, both pairs being formed by portions of the top- and backsheets 3, 4 extending outward beyond a peripheral edge of the core 5.

The diaper 1 is composed of a front waist region 8, a rear waist region 9 and a crotch region 10. Though not shown, the side flaps 6 and/or the end flaps 7 are highly flexible and may be formed also by a suitable material other than the material for the topsheet 3 and/or the backsheet 4. In the crotch region 10, the side flaps 6 are formed with cutouts 11 to define leg-holes. Along curved side edges of these cutouts 11, elastic members 12 having rubber elasticity and comprising a plurality of elastic string or strands are secured under extension between the top- and backsheets 3, 4 by means of a hot melt adhesive 70 as will be described later. In the front and rear waist regions 8, 9, the end flaps 7 are also provided with elastic members 13A, 13B having rubbery elasticity. These elastic members 13A, 13B are also secured under extensions to the top- and backsheets 3, 4 by means of a hot melt adhesive (not shown). It should be understood that, in the diaper 1, the elastic members 13A, 13B may be eliminated in one of the front and rear waist regions 8, 9.

The topsheet 3 is provided on its transversely opposite side edges with barrier flaps 15 normally biased by elastic members 14 under extension. When the diaper 1 is worn and bent toward front and rear directions contraction of the elastic members 14 functions to uprise the barrier flaps 15 on the upper surface of the topsheet 3 and prevents bodily discharges on the topsheet 3 from flowing outward of the diaper and leaking sideways. The barrier flaps 15 have proximal edges 15a and distal edges 15b wherein the proximal edges 15a are joined between the respective side edges of the core 5 and the elastic members 12 by means of well known joining means (not shown) such as a hot melt adhesive or heat-welding. While longitudinally opposite ends of the barrier flaps 15 are collapsed outward away from the center line 2 and bonded to the topsheet 3 in such a collapsed state in FIG. 1, it is also possible to collapse these ends toward the center line 2 and join them to the topsheet 3 as well.

The core 5 is so-called semi-rigid and interposed in a substantially fixed state between the top- and backsheets 3, 4. As a means for such fixation, the well known hot melt adhesive coating in an appropriate pattern (not shown) is preferably used. In the longitudinal direction as well as in the transverse direction of the diaper 1, the core 5 preferably has a stiffness of 1–30 gf·cm (10–30 mN·cm) as measured in accordance with JIS P-8125 so that the elastic members may present a desired tensile stress.

Figure 2:
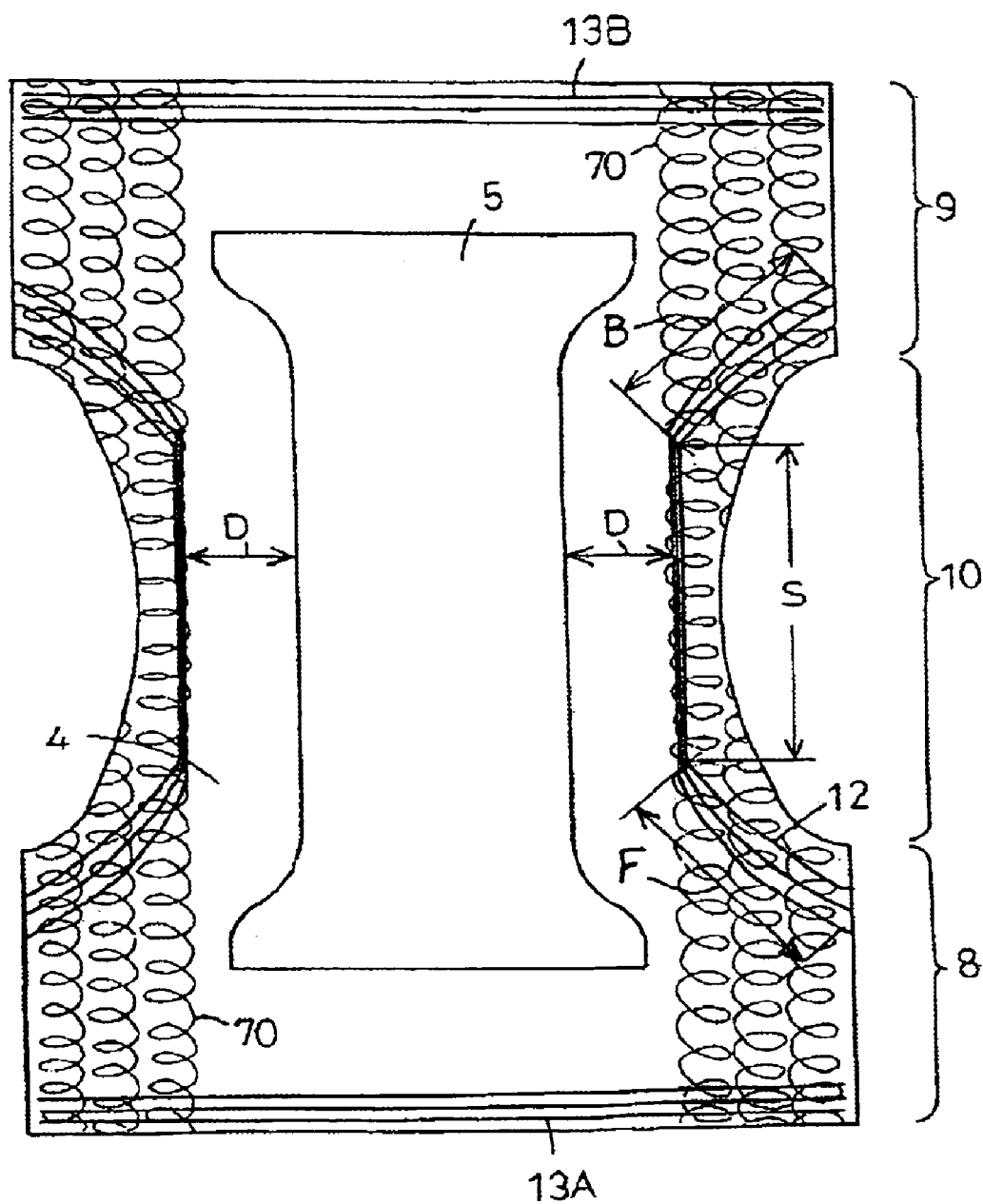
FIG. 2 is a plan view illustrating relative positions of a backsheet, a core and elastic members associated with leg-holes.

FIG. 2 is a plan view illustrating relative positions of the backsheet 4, the core 5 and the respective elastic members 12, 14 in the diaper 1.

A plurality of the elastic members 12 are converged substantially in a single bundle in a middle zone (first elastic zone) S of the crotch region 10 and progressively diverged from this middle zone S toward front and rear side edge zones (second and third elastic zones) F, B in order to assure that the tensile stress in the middle zone S is not higher than that in the front and rear side edge zones F, B. The described "... tensile stress in the middle zone S is not higher ..." used herein means that the tensile stress in the middle zone S is substantially equal to or lower than in the front and rear side edge zones F, B. Under this requirement, length of the middle zone S is at least 30 mm, preferably 50–150 mm; tensile stress in the middle zone S is at least 30 g/25 mm width (300 mN/25 mm width), preferably 50–200 g/25 mm width (500–2000 mN); tensile stress in the front and rear side edges F, B is at least 50 g/25 mm width, preferably 80–230 mm width (800–2300 mN/25 mm width). The values of the tensile stress are those obtained on test pieces with 25 mm in width cut off from the side flap 6 mainly in the elastic members and stretched by 88.9%. Distance D between the elastic members 12 and the side edge of the core 5 in the middle zone S is at least 10 mm, preferably 15–50 mm. The maximum dimension between each pair of the adjacent elastic members 12 in the front and rear side edge zones F, B is 3–15 mm.

On the transversely opposite side edges of the rear waist region 9, the absorbent structure 1A is provided with tape fastener 17 as shown in FIG. 1 to connect the rear waist region 9 to the front waist region 8 so that the absorbent structure 1A can be used as the diaper 1.

While contraction of the elastic members 12 in the diaper 1 generates a plurality of gathers along the middle zones S as well as along the front and rear side edge zones F, B, the tensile stress of the elastic members 12 along the middle zones S is not so high that the number of the gathers and the depth of the gathers trough are equal to or less than those in the front and rear side edges zones F, B. With a consequence, the diaper 1 comes in close in contact with the wearer's skin in the wearer's crotch region without formation of any significant gap between the wearer's skin and the gathers. In this way, there is no anxiety that leak of bodily discharges might occur in the crotch region 10 of the diaper 1, in particular, beyond the middle zones S thereof.

The unique arrangement that the elastic members 12 are spaced from the respective side edges of the core 5 by the distance D along the middle zones S of the diaper 1 and have relatively low tensile stress advantageously restricts a possibility that contraction of the elastic members 12 in the zones S might affect the core 5 as well as the barrier flaps 15. For example, it is not apprehended that contraction of the elastic members 12 in the zones S might twist, deform or crease the core 5 or obstruct the barrier flaps 15 to uprise. Furthermore, there is no anxiety that the absorbent structure 1A might be displaced from its proper position by following stretch or contraction of the elastic members 12 due to a movement of the wearer's legs.

Figure 3:
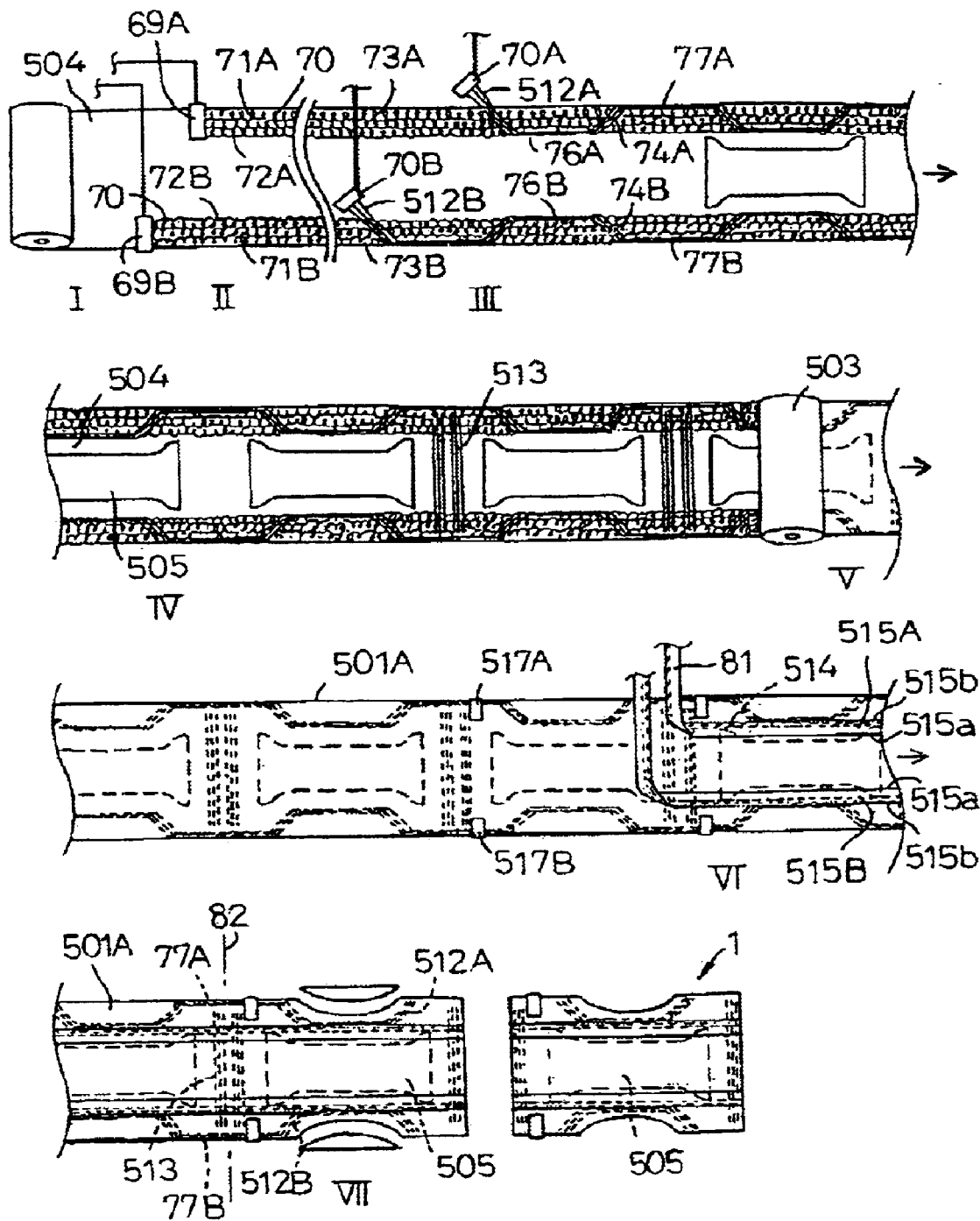
FIG. 3 is a diagram schematically illustrating a process for making the diaper.

(2) A process for placement of the elastic members associated with leg-holes on the diaper as a specific embodiment of the disposable absorbent wearing article:

FIG. 3 is a process diagram schematically illustrating a process for making the diaper 1 provided with the absorbent structure 1A. In the step I, first web 504 made of a continuous liquid-impervious plastic film is supplied to the process at a given rate from the left as viewed in the diagram.

In the step II, a plurality of streaks of a hot melt adhesive 70 are discharged from nozzles 69A, 69B onto transversely opposite side edges of the first web 504 drawing a spiral pattern and providing a first adhesive zone 71A and a second adhesive zone 71B.

In the step III, a plurality of first continuous elastic members 512A and a plurality of second continuous elastic members 512B are fed under extension, by first and second traverse means 70A, 70B reciprocating in a direction orthogonal to the direction in which the first web 504 is being fed, onto the first and second adhesive zones 71A, 71B of the first web 504 so that the respective elastic members may be kept spaced from one another. The first and second continuous elastic members 512A, 512B fed in this manner extend across the respective adhesive zones 71A, 71B beyond respective inner side edges 72A, 72B and respective outer side edges 73A, 73B of the first and second adhesive zones 71A, 71B so as to describe substantially sinusoidal curves along the respective adhesive zones 71A, 71B. Respective first zones 74A, 74B of the first and second continuous elastic members 512A, 512B associated with the leg-holes lying on the respective adhesive zones 71A, 71B are fixed to these adhesive zones 71A, 71B and respective second zones 76A, 76B of the first and second continuous elastic members 512A, 512B associated with the leg-holes extending outward beyond the respective inner side edges 72A, 72B of the adhesive zones 71A, 71B are contractibly shifted toward the respective adhesive zones 71A, 71B so that these second zones 76A, 76B may be fixed to the respective adhesive zones 71A, 71B. The second zones 76A, 76B are converged in single bundles, respectively.

In the step IV, absorbent cores 505 are disposed on the first web 504 in such zones as defined at given intervals in the longitudinal direction of the first web 504 and a plurality of elastic members 513 associated with the waist-hole extending in the transverse direction of the first web 504 are bonded in an elongated state to the first web 504 in the zones defined between each pair of the adjacent cores 505, 505.

In the step V, a second web 503 formed of continuous liquid-pervious sheet is placed upon and bonded to the first web 504 so as to cover the cores 505 and the elastic members 513 associated with the waist-hole to obtain a laminate 501A. Though not illustrated, the first web 504 and the second web 503 may be bonded to each other using a hot melt adhesive or welding technique.

In the step VI, elastically stretchable first and second continuous flap members 515A, 515B are bonded, while applying tension in the advancing direction of the second web 503 being fed, to the upper surface of the second web 503 along transversely opposite side edges of the laminate 501A. Each of the first and second continuous flap members 515A, 515B comprises a narrow web 81 having transversely opposite side edges 515a and 515b. The one side edge 515b is provided with elastic members 514 bonded under extension and the other side edge 515a is secured to the second web 503. Tape fasteners 517A, 517B are attached to the laminate 501A in given zones along its transversely opposite side edges.

In the step VII, the side edges of the laminate 501A are cut off in a semicircular shape along the first and second continuous elastic members 512A, 512B associated with the leg-holes. Then the laminate 501A is cut along lines 82 transversely extending between each pair of the adjacent cores 505, 505 so as to bisect a plurality of elastic members 513 associated with the waist-hole in two direction of the second web 503 being fed and thereby individual diapers 1 are obtained.

Figure 4:
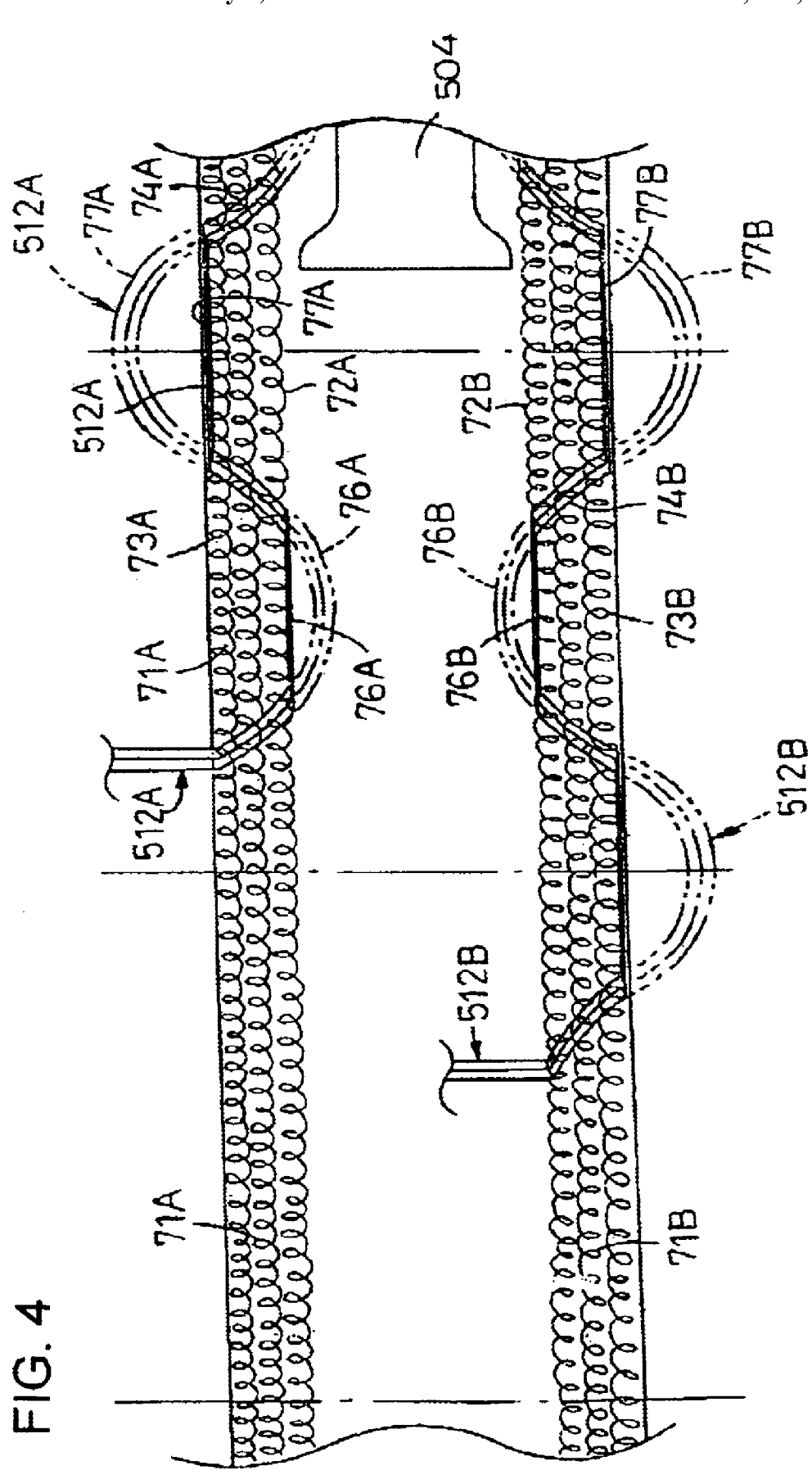
FIG. 4 is a partially-enlarged diagram illustrating steps III and IV in FIG. 3.

FIG. 4 is a scale-enlarged diagram schematically illustrating the steps III and IV of FIG. 3. Referring to FIG. 4, imaginary lines indicate a manner in which the first and second continuous elastic members 512A, 512B associated with the leg-holes are fed by the respective traverse means 70A, 70B and solid lines indicate state of these members 512A, 512B immediately after they have been fed.

The first and second continuous elastic members 512A, 512B are fed so that these members 512A, 512B extend across the first and second adhesive zones 71A, 71B, respectively, beyond both the inner side edges 72A, 72B and the outer side edges 73A, 73B. After having been fed in this manner, the zones 76A, 76B extending beyond the inner side edges 72A, 72B are contractibly shifted so as to extend rectilinearly along the inner side edges 72A, 72B, respectively. The third zones 77A, 77B extending beyond the outer side edges 73A, 73B also are contractibly shifted so as to extend rectilinearly along the outer side edges 73A, 73B, respectively. These third zones 77A, 77B are also cut when the laminate 501A is cut in the step VII. The third zones 77A, 77B may be either secured or not to the first and second continuous adhesive zones 71A, 71B, respectively. If these zones 77A, 77B are secured to the adhesive zones 71A, 71B, respectively, these zones are kept to extend rectilinearly along the outer side edges 73A, 73B even after having been cut and if these zones 77A, 77B are not bonded to the adhesive zones 71A, 71B, respectively, these zones 77A, 77B further contract as these zones are cut. FIGS. 1–3 shows the diaper 1 in which the third zones 77A, 77B have further contracted.

The main stock materials used in the process for making the article as has been described correspond to the respective members in the diaper 1 shown in FIGS. 1 and 2 as follows: the first continuous web 504 and the second continuous web 503 correspond to the backsheet 4 and topsheet 3; the core 505 corresponds to the core 5; the first and second continuous elastic members 512A, 512B associated with the leg-holes correspond to the elastic members 12 associated with the leg-holes; the fixed zones 74A, 74B of the first and second elastic members 512A, 512B associated with the leg-holes correspond to the front and back side edge zones 12F, 12B; the zones 76A, 76B of the first and second elastic members 512A, 512B extending along the inner side edges 72A, 72B of the first and second continuous adhesive zones 71A, 71B correspond to the middle side edge zones 12S of the elastic members 12 associated with the leg-holes; the third zones 77A, 77B of the first and second continuous elastic members 512A, 512B associated with the leg-holes extending along the outer side edges 73A, 73B of the first and second continuous adhesive zones 71A, 71B without being bonded to these adhesive zones 71A, 71B contract and define ends of the front and back side edge zones 12F, 12B of the elastic members 12 associated with the leg-holes; and the elastic members 513 associated with the waist-hole corresponding to the front and rear elastic members 13A, 13B associated with the waist-hole.

For the absorbent structure 1A and the diaper 1 made in the manner as has been described above, it is possible to ensure that the second zones 76A, 76B of the first and second continuous elastic members 512A, 512B associated with the leg-holes extending beyond the inner side edges 72A, 72B of the first and second adhesive zone 71A, 71B have the tensile stress decreased with respect to the initial tensile stress thereof in the course of being fed, specifically, equal to or less than the tensile stress presented by the fixed first zones 74A, 74B of the elastic members 512A, 512B, depending on the extension with which the first and second continuous elastic members 512A, 512B are fed onto the first web 504. For example, these elastic members 512A, 512B may be fed so that a stretch ratio of these elastic members 512A, 512B gradually increases as these elastic members 512A, 512B get nearer to the center line bisecting the width of the first web 504 and then the second zones 76A, 76B extending beyond the inner side edges 72A, 72B of the first and second adhesive zones 71A, 71B contract in order to achieve such effect. The elastic members 512A, 512B are converged and considerably spaced from the curved side edges of the core 505 surrounding the thighs. The diaper 1 having such first and second continuous elastic members 512A, 512B associated with the leg-holes corresponds to the diaper shown by FIG. 1 as the typical embodiment.

While this invention has been described on the basis of the disposable diaper 1 as the one embodiment, this invention is applicable also to the other disposable absorbent wearing article such as pad for incontinent or sanitary napkin. The elastic members 12 associated with the leg-holes are attached to the side flaps 6 of such article and these side flaps 6 may be formed by the topsheet 3 and/or the backsheet 4 or may be formed by a separate sheet replacing at least one of these sheets 3, 4. Furthermore, the coating pattern of the hot melt adhesive 70 for attachment of the elastic members 12, 512A, 512B associated with the leg-holes is not limited to the spiral pattern as illustrated and the other pattern such as appropriate curves or straight lines may be used. In addition, the first web 504 and the second web 503 may be coated along the side edges thereof with the adhesive in the form of many small dots which define substantially continuous adhesive zones.

The elastic members associated with the leg-holes present the tensile stress not higher along the middle side edge zones than along the front and rear side edge zones in the crotch region. Accordingly, the number as well as the depth of the gathers formed along the middle side edge zones are equal to or less than those along the front and rear side edge zones. Along the middle side edge zones, the wearing article is held in close contact with the thighs without leaving any significant gap between the wearer's skin and the gathers which might cause leak of body fluids. In spite of the arrangement that the elastic members associated with the leg-holes extending along the middle side edge zones are considerably spaced from the side edges of the core, it is not likely that stretch and contraction of the elastic members associated with the leg-holes along the middle side edges might cause the core to be twisted and/or cause the article worn to slip down along the thighs.

The process according to this invention for placement of the elastic members associated with the leg-holes allows the disposable absorbent wearing article to be continuously made in the unique manner such that the elastic members associated with the leg-holes present the tensile stress not higher along the middle side edges than along the front and rear side edges of the wearing article's crotch region.

What is claimed is:

1. A disposable absorbent wearing article having a longitudinal direction and a transverse direction orthogonal to said longitudinal direction, comprising an absorbent structure including a liquid-pervious topsheet, a liquid-impervious backsheet, a liquid-absorbent core disposed therebetween and a pair of side flaps extending outward from transversely opposite side edges of said core, a plurality of elastic members associated with leg-holes being placed on cutouts formed in said side flaps to surround the thighs of a wearer, said disposable absorbent wearing article further comprising:

said plurality of elastic members associated with leg-holes being converged substantially into respective single bundles along first elastic zones each extending over a given length of said crotch region in said longitudinal direction of said article and being spaced one from another along second and third elastic zones extending from said first elastic zone along respective side edges of said front and rear waist regions over a given length; and said elastic members associated with the leg-holes having a tensile stress not higher in said first elastic zone than in said second and third elastic zones and said first, second and third elastic zones of said elastic members associated with the leg-holes are contiguous one to another.

2. The article according to claim 1, wherein said core has a stiffness of 1–30 gf·cm (10–300 mN·cm) in said longitudinal and transverse directions.

3. The article according to claim 1, wherein said elastic members associated with the leg-holes are respectively spaced in said first elastic zones from said side edges of said core at least by 10 mm.

4. The article according to claim 1, wherein said elastic members associated with the leg-holes in said second and third elastic zones are progressively diverged as those elastic members extend in said front and rear waist regions.

* * * * *